United States Patent [19]

Ita et al.

[11] 4,395,556
[45] Jul. 26, 1983

[54] NITROBENZOFURAN DERIVATIVES

[75] Inventors: Callixtus E. Ita, South River, N.J.; Anthony F. Heald, Glen Mills, Pa.; Peter Egli, Titusville, N.J.

[73] Assignee: E. R. Squibb & Sons, Inc., Princeton, N.J.

[21] Appl. No.: 345,883

[22] Filed: Feb. 4, 1982

[51] Int. Cl.³ .............................................. C07D 271/12
[52] U.S. Cl. ..................................... 548/126; 436/56; 436/546; 436/800; 436/826; 546/199
[58] Field of Search ......................................... 548/126

[56] References Cited

U.S. PATENT DOCUMENTS

| | | | |
|---|---|---|---|
| 3,524,861 | 8/1970 | Hackmann et al. | 548/126 |
| 3,655,661 | 11/1972 | Wasson | 548/126 |
| 4,046,889 | 9/1977 | Ondetti et al. | 424/244 |
| 4,179,568 | 12/1979 | Cohen et al. | 546/208 |

FOREIGN PATENT DOCUMENTS

| | | | |
|---|---|---|---|
| 1070094 | 5/1967 | United Kingdom | 548/126 |
| 819103 | 5/1979 | U.S.S.R. | 548/126 |

OTHER PUBLICATIONS

Birkett et al., "The Reactivity of SH Groups with a Fluorogenic Reagent", FEBS Letters, vol. 6, No. 4, Feb. 1970, pp. 346-348.

*Primary Examiner*—Donald G. Daus
*Assistant Examiner*—Chabi C. Kalita
*Attorney, Agent, or Firm*—Lawrence S. Levinson; Burton Rodney

[57] ABSTRACT

Nitrobenzofurazan derivatives having the formula

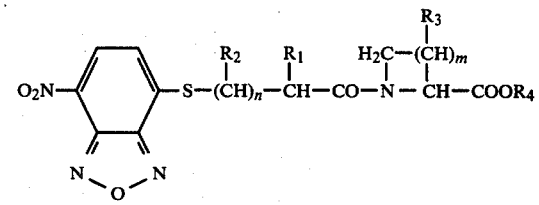

are provided wherein $R_1$ and $R_2$ each is hydrogen, lower alkyl or phenyl-lower alkyl; $R_3$ is hydrogen, hydroxy or lower alkyl; $R_4$ is hydrogen or lower alkyl; m is 2 or 3; and n is 0, 1 or 2; these compounds are useful analytical tools.

4 Claims, No Drawings

NITROBENZOFURAN DERIVATIVES

BACKGROUND OF THE INVENTION

U.S. Pat. No. 4,046,889, issued Sept. 6, 1977 describes a group of thioalkanoyl derivatives of azetidine-, pyrrolidine- and piperidinecarboxylic acid derivatives which are useful as inhibitors of the conversion of the decapeptide angiotensin I to angiotensin II, and are therefore useful in reducing or relieving angiotensin related hypertension.

Among the compounds described in the abovementioned patent are those having the structural formula

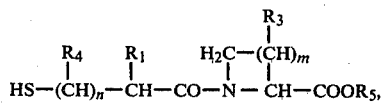

and salts thereof, wherein the variables are as defined hereinafter. These compounds readily convert to the corresponding dimers(through the sulfur atom) and other more polar products in biological fluids such as blood and urine. This conversion presents a problem in running studies to follow the time course of the compounds in the bodies of animals or man.

It is an object of this invention to prevent or minimize the conversion of the compounds illustrated above immediately upon the collection of biological samples containing these compounds, and thus allow for the collection of reliable analytical data.

These and other objectives may be realized by using the method and novel compounds described hereinafter.

SUMMARY OF THE INVENTION

Compounds having the formula

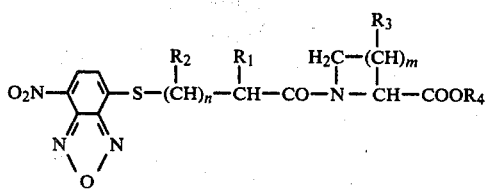

and salts thereof, are useful analytical tools. In formula I, and throughout the specification, the symbols are as defined below:

$R_1$ and $R_2$ each is hydrogen, lower alkyl or phenyl-lower alkyl;
$R_3$ is hydrogen, hydroxy or lower alkyl;
$R_4$ is hydrogen or lower alkyl;
m is 2 or 3; and
n is 0, 1 or 2.

The expression "lower alkyl," as usedthroughout the specification, includes straight and branched chain hydrocarbon radicals from methyl to heptyl, e.g., methyl, ethyl, propyl, isopropyl, butyl, isobutyl, t-butyl, pentyl, isopentyl and the like. Those lower alkyl groups having 1 to 4 carbon atoms, especially those having 1 to 2 carbon atoms are preferred. The preferred phenyl-lower alkyl group is phenylmethyl.

The method of this invention comprises the stabilization of a compound having the formula

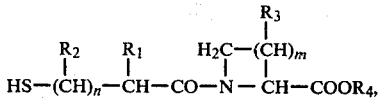

or a salt thereof, in a biological fluid by the addition to the biological fluid of 4-chloro-7-nitrobenzofurazan having the formula

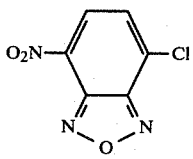

in an amount sufficient to react with all of the compound of formula II.

The 4-chloro-7-nitrobenzofurazan also referred to as 7-chloro-4-nitrobenzo-2-oxa-1,3-diazole may be prepared as described by Boulton et al J. Chem. Soc. B. (1966) 1004.

DETAILED DESCRIPTION OF THE INVENTION

In the development and use of a compound of formula II as an antihypertensive agent, various studies are required to show the time course of the drug in the body. These studies involve the gathering of both animal and human data. It is important to know for different time intervals after administration of the drug how much of the drug is in the blood stream, how much of the drug has been excreted from the body, how much of the drug has been metabolized, etc.

In order to insure the collection of accurate metabolism data, it is essential that conversion of the drug be prevented or minimized immediately upon the taking of a biological sample.

In accordance with the method of this invention, a biological fluid, such as blood or urine, believed to contain a compound of formula II, or a salt thereof, is mixed with the 4-chloro-7-nitrobenzofurazan derivative of formula III. The compounds of formulae II and III react in situ to form the product of formula I, or salt thereof, which is a fluorescent adduct stable in aqueous solution, and allow for accurate time-based quantitative measurements using known analytical techniques, e.g., thin-layer chromatography, thin-layer radiochromatography, high pressure liquid chromatography or gas chromatography.

Pure samples of the compounds of formula I, and salts thereof, must also be synthesized for use as standards in the various analytical techniques. This can be accomplished by reacting a compound of formula II, or a salt thereof, with a 4-chloro-7-nitrobenzofurazan derivative of formula III, in water. The reaction can conveniently be run at room temperature, and can be carried out in an inert atmosphere, e.g., argon or nitrogen. The reaction proceeds most readily in a slightly basic aqueous medium (pH 7.5) and it is, therefore, desirable to add a weak base, such as weak sodium bicarbonate solution, to the reaction mixture.

The starting compounds of formula II, and salts thereof, are known in the art; see, for example, U.S. Pat. No. 4,046,889 issued Sept. 6, 1977. As described therein, the compounds of formula II can be prepared by coupling an acid or ester of the formula

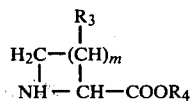

with a haloalkanoic acid of the formula

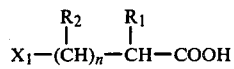

wherein $X_1$ is a halogen, preferably chlorine or bromine. The coupling is accomplished by one of the known procedures in which the haloalkanoic acid is activated, prior to reaction with a compound of formula IV, involving formation of a mixed anhydride, symmetrical anhydride, acid chloride, active ester, or use of Woodward reagent K, EEDQ (N-ethoxycarbonyl-2-ethoxy-1,2-dihydroquinoline) or the like.

The product of this reaction is a compound of the formula

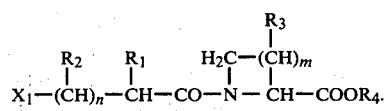

This product is subjected to a displacement reaction with the anion of a thioacid of the formula $$Y-CO-SH \qquad VII$$

wherein Y is lower alkyl, phenyl or phenyl-lower alkyl, yielding a product of the formula

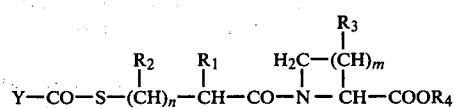

Ammonolysis of a product of formula VIII yields the starting compound of formula II.

Additional processes for the preparation of the starting compounds of formula II are described in U.S. Pat. No. 4,046,889; the disclosure of the patent is incorporated herein by reference.

The compounds of formula I exist in stereoisomeric forms or in racemic mixtures thereof. All of these are within the scope of this invention.

The studies carried out to obtain metabolism data for the compounds of formula II can be run using radioactive analogues of the compounds of formula II. For example, sulfur-35 may be substituted for the sulfur atom in the compound, tritium may be substituted for one or more of the hydrogen atoms, carbon-14 may be substituted for one or more of the carbon atoms, etc. Radioactive analogues are included within the definition of the structural formula II. In the instance wherein a radioactive compound of formula II is being stabilized, the product of formula I will be the corresponding radioactive analogue. Radioactive analogues are included within the definition of structural formula I.

The following examples represent preferred embodiments of this invention.

EXAMPLE 1

(S)-1-[2-Methyl-3-[(4-nitrobenzofurazan-7-yl)thio]-1-oxopropyl]-L-proline

3 Mg of 1-(3-mercapto-2-methyl-1-oxopropyl)-L-proline was placed in a vial and dilute hydrochloric acid (0.1 N, 2 ml) added to dissolve same. 3 Ml of 0.1 M sodium bicarbonate solution was next added and the mixture was mixed in a vortex mixer. Thereafter, 3 ml of 1% (w/v) 4-chloro-7-nitrobenzofurazan in methyl ethyl ketone was added to the mixture, the vial was then closed and mixing was continued. The vial was held under running hot tap water, while shaking the vial, for about 2 minutes. The vial was then allowed to stand for 3 minutes, the organic (upper) layer was removed and was found to contain the title compound. The title compound was found to be fluorescent.

EXAMPLE 2

(S)-1-[2-Methyl-3-[(4-nitrobenzofurazan-7-yl)thio]-1-oxopropyl]-L-proline

700 Mg of 1-(3-mercapto-2-methyl-1-oxopropyl)-L-proline, 700 mg of 4-chloro-7-nitrobenzofurazan (10% excess), 1 g sodium bicarbonate, and 10 ml dichloromethane were stirred at 20° C. for 16 hours. The reaction mixture was put in a 4×30 cm Silicar CC4 column, and eluted with $C_6H_6:CH_3COOH$ (3:1) mixture (v/v).

The title compound was recovered as a syrup (90% purity, 695 mg) and was found to show fluorescence.

EXAMPLE 3

(S)-1-[2-Methyl-3-[(4-nitrobenzofurazan-7-yl]-thio]-1-oxopropyl]-L-proline 2.55 Grams of 1-(3-mercapto-2-methyl-1-oxopropyl)-L-proline was dissolved in 100 ml of water in an erlenmeyer flask. 2.87 Grams of 4-chloro-7-nitrobenzofurazan was dissolved in 100 ml of methyl ethyl ketone. 200 Ml of 0.1 M sodium bicarbonate solution was added to the solution of 1-(3-mercapto-2-methyl-1-oxopropyl)-L-proline and mixed therewith. The solution of 4-chloro-7-nitrobenzofurazan was immediately poured into the mixture. The flask containing the mixture was then put in a hot water bath set at 60° C.; and the mixture was stirred for 5 minutes.

The flask was removed after the 5 minutes and allowed to come to room temperature. The mixture was acidified to pH 2 with 0.2 N.HCl and poured into a separatory funnel. Extraction was done with dichloromethane until the aqueous phase was almost colorless. The crude extract was divided in two and each was purified over the silica gel column. The eluting solvents were (1) chloroform:ethyl acetate:glacial acetic acid (4:5:3) mixture (v/v/v) and (2) dichloromethane.

The eluant was evaporated to dryness in vacuum to yield the title product in the form of a dark yellow syrup (2.47 g) which was found to show fluorescence.

The yield was greatly increased when a solution of 4-chloro-7-nitrobenzofurazan in p-dioxane was used. This was then used as the basis for a trapping and fluorescent assay of 1-(3-mercapto-2-methyl-1-oxopropyl)-L-proline in urine.

What is claimed is:

1. A compound having the formula

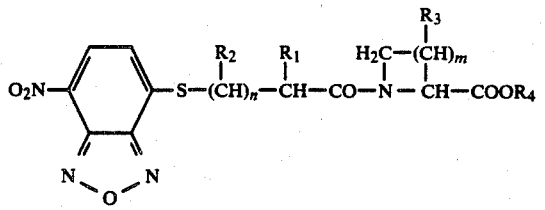

or a salt thereof, wherein $R_1$ and $R_2$ each is hydrogen, lower alkyl or phenyl-lower alkyl; $R_3$ is hydrogen, hydroxy or lower alkyl; $R_4$ is hydrogen or lower alkyl; m is 2 or 3; and n is 0, 1 or 2.

2. A compound in accordance with claim 1 wherein $R_4$ is hydrogen.

3. A compound in accordance with claim 1 wherein $R_1$ is methyl, n is 1, m is 2 and $R_2$ and $R_3$ are each hydrogen.

4. The compound in accordance with claim 1 having the name 1-[2-methyl-3-[(4-nitrobenzofurazan-7-yl)thio]-1-oxopropyl]-L-proline.

* * * * *

UNITED STATES PATENT AND TRADEMARK OFFICE
CERTIFICATE OF CORRECTION

PATENT NO. : 4,395,556
DATED : July 26, 1983
INVENTOR(S) : Callixtus E. Ita et al.

It is certified that error appears in the above—identified patent and that said Letters Patent is hereby corrected as shown below:

Title Page, the title should read --Nitrobenzofurazan-7-yl thio-1-oxo Alkyl Prolines--.
Column 1, the title should read --Nitrobenzofuran-7-yl thio-1-oxo Alkyl Prolines--.
Column 6, line 2, delete "or 3".

Signed and Sealed this

Fourth Day of September 1984

[SEAL]

Attest:

GERALD J. MOSSINGHOFF

Attesting Officer

Commissioner of Patents and Trademarks